(12) United States Patent
Kim

(10) Patent No.: US 11,028,395 B2
(45) Date of Patent: Jun. 8, 2021

(54) TNF-ALPHA-BINDING APTAMER, AND THERAPEUTIC USE FOR SAME

(71) Applicant: BIOIS CO., LTD., Seoul (KR)

(72) Inventor: Sung-Chun Kim, Seoul (KR)

(73) Assignee: BIOIS CO., LTD., Seoul (KR)

( * ) Notice: Subject to any disclaimer, the term of this patent is extended or adjusted under 35 U.S.C. 154(b) by 230 days.

(21) Appl. No.: 16/344,107

(22) PCT Filed: Oct. 24, 2016

(86) PCT No.: PCT/KR2016/011981
§ 371 (c)(1),
(2) Date: Apr. 23, 2019

(87) PCT Pub. No.: WO2018/079864
PCT Pub. Date: May 3, 2018

(65) Prior Publication Data
US 2019/0323012 A1    Oct. 24, 2019

(51) Int. Cl.
*C12N 15/11* (2006.01)
*C12N 15/115* (2010.01)
*C12N 15/10* (2006.01)

(52) U.S. Cl.
CPC ........ *C12N 15/115* (2013.01); *C12N 15/1048* (2013.01); *C12N 2310/16* (2013.01); *C12N 2310/31* (2013.01); *C12N 2310/32* (2013.01); *C12N 2310/321* (2013.01); *C12N 2310/334* (2013.01); *C12N 2310/335* (2013.01); *C12N 2310/351* (2013.01)

(58) Field of Classification Search
CPC .............. C12N 15/115; C12N 2310/16; C12N 2310/351
See application file for complete search history.

(56) References Cited

FOREIGN PATENT DOCUMENTS

| JP | 2011-155913 A | 8/2011 |
|---|---|---|
| KR | 10-1090177 B1 | 12/2011 |
| KR | 10-1261589 B1 | 5/2013 |
| KR | 10-2015-0140669 A | 12/2015 |
| WO | WO-2013-185241 A1 | 12/2013 |

OTHER PUBLICATIONS

International Search Report from corresponding PCT Application No. PCT/KR2016/011981, dated Jul. 12, 2017, with English Translation.

*Primary Examiner* — Ekaterina Poliakova-Georgantas
(74) *Attorney, Agent, or Firm* — Harness, Dickey & Pierce, P.L.C.

(57) ABSTRACT

The present invention relates to a TNF-α-binding RNA aptamer disclosed in SEQ ID NO: 1 or SEQ ID NO: 2, and to the therapeutic use thereof.

13 Claims, 9 Drawing Sheets

Specification includes a Sequence Listing.

SEQUENCE LISTING

```
<160> NUMBER OF SEQ ID NOS: 2

<210> SEQ ID NO 1
<211> LENGTH: 61
<212> TYPE: RNA
<213> ORGANISM: Artificial Sequence
<220> FEATURE:
<223> OTHER INFORMATION: Aptamer

<400> SEQUENCE: 1
gggaggacga ugcggccacu ggcuaggaac ucgaguacug ggugggcagac gacucgcccg    60 a                                                                     61

<210> SEQ ID NO 2
<211> LENGTH: 66
<212> TYPE: RNA
<213> ORGANISM: Artificial Sequence
<220> FEATURE:
<223> OTHER INFORMATION: Aptamer

<400> SEQUENCE: 2
gcggaagcgu gcugggcccg gcuugcaggu cgccgaaaug accgcacaca uaacccagag    60
gucgau                                                                66
```

TNF-ALPHA-BINDING APTAMER, AND THERAPEUTIC USE FOR SAME

CROSS-REFERENCE TO RELATED APPLICATIONS

This application is a national phase application of PCT Application No. PCT/KR2016/011981, filed on 24 Oct. 2016. The entire disclosure of the application identified in this paragraph is incorporated herein by reference.

FIELD

The present invention relates to an aptamer specifically binding to TNF-α and to the therapeutic use thereof.

BACKGROUND

TNF-α is a proinflammatory cytokine that is secreted by cells of the immune system including macrophages and monocytes and reacts with cells of the immune system, and abnormal overexpression thereof mediates various diseases such as sepsis, infectious diseases, autoimmune diseases, and graft rejection, as well as inflammatory reactions (Annu. Rev. Immunol. 10:411-452, 1992; Annu. Rev. Med. 45:491-503, 1994).

For these reasons, various antibody drugs targeting TNF-α have been developed. Representative examples of antibody drugs targeting TNF-α include etanercept (Enbrel™), infliximab (Remicade™), adalimumab (Humira™), certolizumab pegol (Cimzia™) and the like. However, it has been reported that etanercept inhibits the secretion of TNF-α in THP-1 cells treated with LPS but may overexpress cell-bound TNF-α about 6 times to thus cause side effects (Int Immunopharmacol. 8(5):679-87, 2008), infliximab is a chimeric antibody that has a mouse variable domain and a human IgG$_1$ invariable domain, which undesirably causes ADCC (antibody-dependent cellular cytotoxicity) and CDC (complement-dependent cytotoxicity), and certolizumab pegol is a pegylated humanized antibody, a pegylated protein of which has been observed in animal experiments to cause immunogenic responses and also to form vacuoles due to accumulation in the kidney cells (Bioconjug. Chem. 19; 24(6):915-25, 2013).

Thus, the development of drugs having better characteristics targeting TNF-α is still required.

An aptamer is a nucleic-acid ligand capable of specifically binding to a target protein, like the antibody. Since 2004, the US FDA approved Macugen, which targets vascular endothelial growth factor (VEGF), as a therapeutic agent for senile macular degeneration, the development of therapeutic agents using aptamers has been active worldwide (Gene Ther. 14(4): 283-291, 2007).

Aptamer therapeutic agents have various advantages when compared with antibody therapeutic agents, and aptamers are small and simple molecules compared to antibodies, thus enabling chemical synthesis thereof and facilitating necessary chemical modification, and moreover, increasing selectivity and affinity in vitro using SELEX technology (Systematic Evolution of Ligands by EXponential enrichment, Science 249 (4968):505-510, 1990; Methods Enzymol. 267:275-301, 1996; Methods Enzymol. 318: 193-214, 2000; U.S. Pat. Nos. 5,475,096, 5,270,163, International Patent No. WO 91/19813). Unlike protein antibodies, aptamers are thermally stable and may thus be stored for long periods of time at room temperature. Furthermore, aptamers for toxins may be easily formed rather than polyclonal antibodies therefor, and additionally, aptamers rarely cause in-vivo immune responses, unlike antibody therapeutics. Moreover, antibodies have to be produced in vivo or at the cellular level, whereas aptamers are capable of being prepared entirely in vitro, making it easy to adjust the pharmacokinetic and pharmacodynamic properties thereof through chemical modification.

This suggests that the use of an aptamer rather than an antibody may lead to the development of a therapeutic agent that is favorable in terms of efficacy and safety.

The present invention discloses an aptamer specifically binding to TNF-α and the therapeutic use thereof.

SUMMARY

Technical Problem

An objective of the present invention is to provide an aptamer specifically binding to TNF-α.

Another objective of the present invention is to provide the therapeutic use of the aptamer.

The other or specific objectives of the present invention will be described below.

Technical Solution

The present inventor(s) have ascertained that, as is apparent from the following examples, a single-stranded RNA library was prepared from a DNA library, single-stranded RNA binding to TNF-α was separated from each group using SELEX technology to thus identify the sequence thereof, an RNA aptamer of SEQ ID NO: 1 ("ATK001") and an RNA aptamer of SEQ ID NO: 2 ("ATK007"), having high binding affinity to TNF-α, were selected from the above RNA through a plate-based binding assay, and the binding affinity of these aptamers to TNF-α was measured through SPR (Surface Plasmon Resonance) and gel retardation, and moreover, the binding capability thereof to TNF-α was compared and evaluated with the binding capability to ErbB2, ErbB3 and IGF-BP1 through an SPR assay, whereby the binding specificity to TNF-α was confirmed. Furthermore, when the ATK001 and ATK002 aptamers were used for the treatment of SK-HEP1 cells, a liver cancer cell line, with recombinant human TNF-α that causes cell damage, the expression of acute-phase proteins such as hepatoglobin, fibrogen-γ, fibronectin, transferrin, etc., inflammatory cytokines (TNF-α, IL1-β and IL6) and an angiogenic substance (VEGF), the expression levels of which increase quickly upon cell damage, was inhibited.

In the above description, since acute-phase proteins such as hepatoglobin or inflammatory cytokines are proteins whose expression increases in order to protect the cells when damaged, inhibition of the expression of these acute-phase proteins or inflammatory cytokines when TNF-α, which causes cell damage, is used together with the above aptamer indicates that the ATK001 and ATK007 aptamers are effective at inhibiting TNF-α.

Based on such test results, an aspect of the present invention relates to an ATK001 aptamer of SEQ ID NO: 1 below or an ATK007 aptamer of SEQ ID NO: 2 below, which binds to TNF-α, and another aspect of the present invention relates to, as the therapeutic use of the above aptamer, a pharmaceutical composition for TNF-α inhibition or a pharmaceutical composition for the prevention or treatment of disorders or diseases caused by abnormal overexpression of TNF-α, containing the aptamer as an active ingredient.

<SEQ ID NO: 1>
G-G-G-A-G-G-A-C-G-A-U-G-C-G-G-C-C-A-C-U-G-G-C-U-A-G-G-A-A-C-U-C-G-A-G-U-A-C-U-G-G-G-U-G-G-C-A-G-A-C-G-A-C-U-C-G-C-C-C-G-A

<SEQ ID NO: 2>
G-C-G-G-A-A-G-C-G-U-G-C-U-G-G-G-C-C-C-G-G-C-U-U-G-C-A-G-U-C-G-C-C-G-A-A-U-G-A-C-C-G-C-A-C-A-C-A-U-A-A-C-C-C-A-G-A-G-G-U-C-G-A-U

As used herein, the term "TNF-α" refers to any TNF-α present in mammals such as humans and mice, which may be regarded as TNF-α in the function and sequence thereof, and is preferably human TNF-α.

As used herein, the term "aptamer" refers to a nucleic-acid ligand that binds to a target molecule as is known in the art, and preferably a nucleic-acid ligand that 'specifically' binds to a target molecule. Here, 'specifically binding' means binding with a relatively higher affinity to a target molecule than to other molecules in vivo such as a human body or a sample.

As used herein, the term "active ingredient" refers to a component that exhibits the desired pharmaceutical activity when used alone or may exhibit pharmaceutical activity in combination with a carrier that is not itself active.

As used herein, the term "TNF-α inhibition" means that the aptamer of the present invention binds to TNF-α to thus inhibit the intrinsic biological activity of TNF-α. The inhibition of the intrinsic biological activity of TNF-α may effectively lead to the prevention or treatment of a disorder or disease mediated by TNF-α due to abnormal overexpression of TNF-α (or in which abnormal overexpression of TNF-α is deleterious).

As used herein, "disorder or disease caused by abnormal overexpression of TNF-α" is widely interpreted in the art, and means various disorders and diseases known in the art. Specific examples of such disorders and diseases may include respiratory disorders, asthma, allergic and non-allergic asthma, asthma due to infection, asthma due to infection of respiratory syncytial virus (RSV), chronic obstructive pulmonary disease (COPD), airway inflammatory disease, eosinophilia, fibrosis and mucogenesis, cystic fibrosis, pulmonary fibrosis, atopic disorders, atopic dermatitis, urticaria, eczema, allergic rhinitis, allergic gastroenteritis, skin inflammation and/or skin autoimmune diseases, inflammatory and/or autoimmune diseases of the gastrointestinal tract, inflammatory bowel disease (IBD), ulcerative colitis, Crohn's disease, liver inflammation and/or autoimmune diseases, cirrhosis, liver fibrosis, hepatic fibrosis induced by hepatitis B and/or hepatitis C virus, pachydermia, tumors or cancer, hepatocellular carcinoma, glioblastoma, lymphoma, Hodgkin's lymphoma, viral infections, bacterial infections, parasite infections, HTLV-1 infections, and immune responses to vaccination.

More particularly, the disorders and diseases may include rheumatoid arthritis, osteoarthritis, juvenile chronic arthritis, septic arthritis, Lyme arthritis, psoriatic arthritis, reactive arthritis, spondylarthrosis, systemic lupus erythematosus, Crohn's disease, ulcerative colitis, inflammatory bowel disease, insulin-dependent diabetes mellitus, thyroiditis, asthma, allergic diseases, psoriasis, pachydermia, graft-versus-host disease, rejection of organ transplantation, acute or chronic immune disease related to organ transplantation, sarcoidosis, atherosclerosis, disseminated intravascular coagulation, Kawasaki disease, Grave's disease, nephrotic syndrome, chronic fatigue syndrome, Wegener's granulomatosis, Henoch-Schonlein purpura, microscopic vasculitis of the kidney, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's Disease, Alzheimer's Disease, stroke, primary biliary cirrhosis, hemolytic anemia, malignancy, heart failure, myocardial infarction, Addison's disease, sporadic disease, Type I polyglandular deficiency and Type II polyglandular deficiency, Schmidt syndrome, adult (acute) respiratory distress syndrome, alopecia, alopecia areata, seronegative arthropathy, arthropathy, Reiter's disease, psoriatic arthropathy, ulcerative colitic arthropathy, enteropathic synovitis, *chlamydia, yersinia-* and *salmonella-*associated arthropathy, spondyloarthropathy, atheromatous disease/arteriosclerosis, atopic allergy, autoimmune bullous disease, pemphigus vulgaris, pemphigus *foliaceus*, pemphigoid, linear IgA disease, autoimmune haemolytic anemia, Coombs positive haemolytic anemia, acquired pernicious anemia, juvenile pernicious anemia, myalgic encephalitis/Royal Free disease, chronic mucocutaneous candidiasis, giant cell arteritis, primary sclerosing hepatitis, cryptogenic autoimmune hepatitis, acquired immunodeficiency disease syndrome, acquired immunodeficiency-related diseases, hepatitis B, hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective-tissue-disease-associated interstitial lung disease, mixed connective-tissue-disease-associated lung disease, systemic sclerosis-associated interstitial lung disease, rheumatoid-arthritis-associated interstitial lung disease, systemic lupus erythematosus-associated lung disease, dermatomyositis/polymyositis-associated lung disease, Sjodgren's disease-associated lung disease, ankylosing spondylitis-associated lung disease, vasculitic diffuse lung disease, haemosiderosis-associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune-mediated hypoglycemia, type B insulin resistance with acanthosis *nigricans*, hypoparathyroidism, acute immune disease associated with organ transplantation, chronic immune disease associated with organ transplantation, osteoarthrosis, primary sclerosing cholangitis, Type 1 psoriasis, Type 2 psoriasis, idiopathic leucopenia, autoimmune neutropenia, renal disease NOS, glomerulonephritides, microscopic vasculitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis *nodosa*, acute rheumatic fever, rheumatoid spondylitis, Still's disease, systemic sclerosis, Sjogren's syndrome, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, cholestasis, idiosyncratic liver disease, drug-induced hepatitis, non-alcoholic steatohepatitis, allergy and asthma, group B streptococci (GBS) infection, mental disorders (e.g., depression and schizophrenia), Th2-type- and Th1-type-mediated diseases, acute and chronic pain (various forms of pain), cancers such as lung cancer, breast cancer, stomach cancer, bladder cancer, colon cancer, pancreas cancer, ovarian cancer, prostate cancer and rectal cancer, hematopoietic malignancies (leukemia and lymphoma), A-beta-lipoproteinemia, acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, antiphospholipid syndrome, anti-receptor hypersensitivity reactions, aortic and peripheral aneurysms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy-associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture-negative sepsis, cystic fibrosis, cytokine-therapy-associated disorders, dementia pugilistica, demyelinating diseases, dengue hemorrhagic fever, dermatitis, dermatologic conditions, diabetes, diabetes mellitus, diabetic arteriosclerotic disease, diffuse Lewy body disease, dilated congestive cardiomyopathy, disorders of the basal ganglia, Down's syndrome in middle age, drug-induced movement disorders induced by drugs which block CNS dopamine receptors, drug sensitivity, eczema, encephalomyelitis, endocarditis, endocrinopathy, epiglottitis, Epstein-Barr virus infection, erythromelalgia, extrapyramidal and cerebellar disorders, familial hemophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram-negative sepsis, gram-positive sepsis, granulomas due to intracellular organisms, hairy cell leukemia, Hallervorden-Spatz disease, Hashimoto's thyroiditis, hay fever, heart transplant rejection, hemochromatosis, hemodialysis, hemolytic uremic syndrome/thrombolytic thrombocytopenic purpura, hemorrhage, hepatitis (A), His bundle arrhythmias, HIV infection/HIV neuropathy, Hodgkin's disease, hyperkinetic movement disorders, hypersensitivity reactions, hypersensitivity pneumonitis, hypertension, hypothalamic-pituitary-adrenal axis evaluation, idiopathic Addison's disease, idiopathic pulmonary fibrosis, antibody-mediated cytotoxicity, asthenia, infantile spinal muscular atrophy, inflammation of the aorta, influenza A, ionizing radiation exposure, iridocyclitis, uveitis, optic neuritis, ischemia-reperfusion injury, ischemic stroke, juvenile rheumatoid arthritis (JRA), juvenile spinal muscular atrophy, Kaposi's sarcoma, kidney transplant rejection, *legionella*, leishmaniasis, leprosy, lesions of the corticospinal system, lipedema, liver transplant rejection, lymphedema, malaria, malignant lymphoma, malignant histiocytosis, malignant melanoma, meningitis, meningococcemia, metabolic/idiopathic disorders, migraine headaches, mitochondrial multi-system disorders, mixed connective tissue disease, monoclonal gammopathy, multiple myeloma, multiple-system degenerations (Menzel, Dejerine-Thomas, Shy-Drager, and Machado-Joseph), myasthenia gravis, *Mycobacterium avium-intracellulare* infection, *Mycobacterium tuberculosis*, myelodysplasia syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-Hodgkins lymphoma, occlusion of the abdominal aorta and its branches, occlusive arterial disorders, orchitis, epididymitis, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherosclerotic disease, peripheral vascular disorders, peritonitis, pernicious anemia, *Pneumocystis carinii* pneumonia, pneumonia, POEMS syndrome (polyneuropathy, organomegaly, endocrinopathy, monoclonal gammopathy, and skin-change syndrome), post-perfusion syndrome, post-pump syndrome, post-MI cardiotomy syndrome, preeclampsia, progressive supranuclear palsy, primary pulmonary hypertension, radiation therapy, Raynaud's phenomenon and disease, Raynaud's disease, Refsum's disease, regular narrow QRS tachycardia, renovascular hypertension, reperfusion injury, restrictive cardiomyopathy, sarcomas, pachydermia, senile chorea, senile dementia of Lewy body type, seronegative arthropathies, shock, sickle cell anemia, skin allograft rejection, skin-change syndrome, small bowel transplant rejection, solid tumors, specific arrhythmias, spinal ataxia, spinocerebellar degeneration, streptococcal myositis, structural lesions of the cerebellum, subacute sclerosing panencephalitis, syncope, syphilis of the cardiovascular system, systemic anaphylaxis, systemic inflammatory response syndrome, systemic onset juvenile rheumatoid arthritis, T-cell or FAB ALL, telangiectasia, thromboangiitis obliterans, thrombocytopenia, toxicity, transplants, trauma, hemorrhaging, allergies, unstable angina, uremia, urosepsis, urticaria, valvular heart diseases, varicose veins, vasculitis, venous diseases, venous thrombosis, ventricular fibrillation, viral and fungal infections, viral encephalitis/aseptic meningitis, virus-associated hemophagocytic syndrome, Wernicke-Korsakoff syndrome, Wilson's disease, xenograft rejection of any organ or tissue, acute coronary syndromes, acute idiopathic polyneuritis, acute inflammatory demyelinating polyradiculoneuropathy, acute ischemia, adult Still's disease, alopecia areata, anaphylaxis, anti-phospholipid antibody syndrome, aplastic anemia, arteriosclerosis, atopic eczema, atopic dermatitis, autoimmune dermatitis, autoimmune disorder associated with *streptococcus* infection, autoimmune enteropathy, autoimmune hearing loss, autoimmune lymphoproliferative syndrome (ALPS), autoimmune myocarditis, autoimmune premature ovarian failure, blepharitis, bronchiectasis, bullous pemphigoid, cardiovascular disease, catastrophic antiphospholipid syndrome, celiac disease, cervical spondylosis, chronic ischemia, cicatricial pemphigoid, clinically isolated syndrome (CIS) with risk for multiple sclerosis, conjunctivitis, childhood onset psychiatric disorder, chronic obstructive pulmonary disease (COPD), dacryocystitis, dermatomyositis, diabetic retinopathy, diabetes mellitus, disk herniation, disk prolapse, drug-induced immune hemolytic anemia, endocarditis, endometriosis, endophthalmitis, episcleritis, erythema multiforme, erythema multiforme major, gestational pemphigoid, Guillain-Barre syndrome (GBS), hay fever, Hughes syndrome, idiopathic Parkinson's disease, idiopathic interstitial pneumonia, IgE-mediated allergies, immune hemolytic anemia, inclusion body myositis, infectious ocular inflammatory disease, inflammatory demyelinating disease, inflammatory heart disease, inflammatory kidney disease, IPF/UIP, iritis, keratitis, keratoconjunctivitis sicca, Kussmaul disease or Kussmaul-Meier disease, Landry's paralysis, Langerhan's cell histiocytosis, livedo reticularis, macular degeneration, microscopic polyangiitis, ankylosing spondylitis, motor neuron disorders, mucous membrane pemphigoid, multiple organ failure, myasthenia gravis, myelodysplasia syndrome, myocarditis, nerve root disorders, neuropathy, hepatitis, optic neuritis, osteolysis, ovarian cancer, pauciarticular JRA, peripheral artery occlusive disease (PAOD), peripheral vascular disease (PVD), peripheral artery disease (PAD), phlebitis, polyarteritis nodosa (or periarteritis nodosa), polychondritis, polymyalgia rheumatica, poliosis, polyarticular JRA, polyendocrine deficiency syndrome, polymyositis, polymyalgia rheumatica (PMR), post-pump syndrome, primary Parkinsonism, prostate and rectal cancer and hematopoietic malignancies (leukemia and lymphoma), prostatitis, pure red cell aplasia, primary adrenal insufficiency, recurrent neuromyelitis optica, restenosis, rheumatic heart disease, SAPHO (synovitis, acne, pustulosis, hyperostosis, and osteitis), pachydermia, secondary amyloidosis, shock lung, scleritis, sciatica, secondary adrenal insufficiency, silicone-associated connective tissue disease, Sneddon-Wilkinson dermatosis, ankylosing spondylitis, Stevens-Johnson syndrome (SJS), systemic inflammatory response syndrome, temporal arteritis, toxoplasmic retinitis, toxic epidermal necrolysis, transverse myelitis, TRAPS (tumor necrosis factor receptor-associated periodic syndrome), Type II diabetes, urticaria, usual interstitial pneumonia (UIP), vasculitis, vernal conjunctivitis, viral retinitis, Vogt-Koyanagi-Harada syndrome (VKH syndrome), wet macular degeneration, wound healing, yersinia and salmonella-associated arthropathy.

SELEX technology is typically used to select an aptamer specifically binding to a certain target molecule. SELEX is an abbreviation for "Systematic Evolution of Ligands by EXponential enrichment", and the corresponding technique is disclosed in the paper [Science 249 (4968):505-510, 1990], U.S. Pat. Nos. 5,475,096, 5,270,163, and International Patent No. WO 91/19813, and detailed methods for selecting aptamers or the use of appropriate reagents or materials are disclosed in the paper [Methods Enzymol. 267:275-301, 1996], and the paper [Methods Enzymol. 318:193-214, 2000].

This SELEX technology begins with a single-stranded RNA or DNA library, in which the oligonucleotides of such a nucleic acid library generally comprise a random sequence between 5' and 3' ends and a known sequence common between all the oligonucleotides of the library at the 5' and 3' ends. This known sequence includes a sequence to which forward/reverse primers bind, a promoter sequence of RNA polymerase, a restriction enzyme recognition sequence for manipulation such as cloning, etc. Since the random sequence is usually composed of 20 to 50 nucleotides, the entire length of the oligonucleotide including the 5' end and the 3' end is usually 30 to 80 nucleotides, and preferably 40 to 60 nucleotides. The synthesis of such oligonucleotides is well known in the art, and these methods include solid-phase oligonucleotide synthesis techniques, solution-phase synthesis techniques such as triester synthesis, and the like. Detailed contents thereof are disclosed in the paper [Nucl. Acid Res. 14:5399-5467, 1986], the paper [Tet. Lett. 27:5575-5578, 1986], the paper [Nucl. Acid Res. 4:2557, 1977], the paper [Lett., 28:2449, 1978], etc. It is also possible to use commercially available automated DNA synthesizers and to obtain nucleic acid libraries including $10^{14}$ to $10^{16}$ oligonucleotides sufficient to apply SELEX technology when using such a synthesizer. When an RNA library is used as the nucleic acid library, the RNA library may be obtained by transcribing a DNA library with an RNA polymerase such as T3, T4, or T7.

The nucleic acid library thus obtained is used to perform the SELEX process. The SELEX process includes (a) bringing the nucleic acid library into contact with a target molecule under conditions suitable for binding to the target molecule, (b) obtaining a target molecule-nucleic acid complex by separating a nucleic acid (oligonucleotide) specifically binding to the target molecule from unbound nucleic acids, and (c) amplifying the nucleic acid from the target molecule-nucleic acid complex. The contact step, the binding step (of obtaining a target molecule-nucleic acid complex) and the amplification step may be repeated for at least 1 cycle, and preferably 5 cycles or more, in order to select a nucleic-acid ligand having higher specificity and binding capability to the target molecule. When the nucleic acid library is an RNA library, cDNA is synthesized before the amplification of step (c), amplified, and then transferred to obtain an RNA ligand. A sequencing process may also be implemented by cloning each nucleic-acid ligand after amplification.

In embodiments of the present invention, a plate-based binding assay is also used, in addition to the SELEX process, thus selecting RNA aptamers of SEQ ID NOS: 1 and 2 specific to TNF-α.

For reference, some improved technologies pertaining to the SELEX process are well known in the art. Examples thereof include Counter-SELEX technology for increasing specificity to a target molecule (Science 263(5152):1425-1429, 1994), Toggle SELEX technology pertaining to non-clinical animal experiments in the development of aptamer therapeutics (Mol Ther 4(6):567-573, 2001), Spiegelmer technology using target molecule and aptamer enantiomers (Chem Biol 9(3):351-359, 2002), and the like.

Many documents are cited in this specification, and all of the cited documents are considered part of this specification, unless expressly stated otherwise.

In the present invention, the aptamer may be the single-stranded RNA itself disclosed in SEQ ID NO: 1 or 2, or may be an aptamer in which the above RNA aptamer is chemically modified at the sugar position, phosphate position, base position, and 5' end and/or 3' end of the ribonucleotide.

It is well known in the art that wild-type RNA or DNA is easily degraded by an endonuclease or exonuclease in vivo. The chemically modified aptamer may improve stability in vivo, thus increasing the in-vivo half-life to ultimately improve the pharmacodynamic and pharmacokinetic properties, and also imparting resistance to chemical and physical degradation to thereby increase storage stability.

The modification at the sugar position means that at least one hydroxyl group (OH group) of the sugar of at least one ribonucleotide of the RNA aptamer of the present invention is modified with a halogen group, an aliphatic group, an ether group, an amine group or the like. Preferably, the 2'-OH group is modified with any one of OMe, O-alkyl, O-allyl, S-alkyl, S-allyl, and halogen, and more preferably with 2'-deoxy, 2'-F, 2'-NH$_2$, 2'-OMe, or combinations thereof.

More preferably, in the following examples, 2'F-CTP and 2'F-UTP were used to prepare RNA aptamers of SEQ ID NOS: 1 and 2 according to the present invention, in which all C and U of the RNA aptamers of SEQ ID NOS: 1 and 2 according to the present invention are fC (2'-F-modified C) and fU (2'-F-modified U).

Details of the sugar modified at the 2' position, including the production method thereof, are known in the art, and for example, reference may be made to the paper [Sproat, et al, Nucl. Acid Res. 19:733-738(1991)], the paper [Cotten, et al, Nucl. Acid Res. 19:2629-2635(1991)], the paper [Hobbs, et al, Biochemistry 12:5138-5145(1973)] and the like.

Regarding the selection of an aptamer having high affinity to a target molecule among the aptamers including the modified sugars through SELEX technology, reference may be made to U.S. Pat. Nos. 5,660,985, 5,756,703, 5,580,737, etc. In particular, U.S. Pat. No. 5,580,737 discloses a method of selecting a nucleic-acid ligand specific to a target molecule, including 2'-NH$_2$—, 2'-F-, or 2'-OMe-modified nucleotides.

Also, the modification at the sugar position may be accomplished using sugar analogues that may substitute for ribose. Examples of the analogues may include α-anomeric sugars, epimeric sugars such as arabinose, xylose or lyxose, pyranose sugars, furanose sugars, sedoheptuloses, and abasic nucleoside analogues such as methyl riboside, and more specific examples thereof are disclosed in International Patent No. WO 2011/130195.

The RNA aptamer may be synthesized using T3, T4, T7, SP6 RNA polymerase or mutant T7 polymerase, and the RNA aptamer including 2'-modified nucleotide may be synthesized, in particular, using mutant polymerase. Examples of the mutant polymerase able to synthesize the RNA aptamer including 2'-modified nucleotide may include mutant T7 polymerase Y639F, mutant T7 polymerase Y639F/H784A, mutant T7 polymerase H784A, and the like, which are known in the art. The T7 polymerase Y639F, which is a mutant polymerase in which a tyrosine residue at the 639 position is replaced with phenylalanine, is known in the art to synthesize RNA including 2'-modified nucleotide using 2'-deoxy, 2'-NH$_2$—, or 2'-F-NTP as a substrate (Science, 286:2305-2308, 1999), and is actually widely used in the art in order to synthesize RNA including 2'-modified nucleotide. However, the mutant T7 polymerase Y639F is limited with regard to the use, as a substrate, of 2'-modified NTP (especially 2'-modified GTP) having 2'-OMe, 2'-N$_3$ or the like (Nucleic Acids Res., 2002, 30(24):138). A mutant T7 polymerase Y639F/H784A, which is a double mutant polymerase in which histidine at the 784 position is replaced with an alanine residue, in addition to the Y639F mutant RNA polymerase, may use 2'-modified NTP having 2'-OMe, 2'-N$_3$ or the like as a substrate, and a single mutant T7 polymerase H784A in which histidine at the 784 position is replaced with alanine residue may use 2'-modified NTP having 2'-OMe, 2'-N$_3$ or the like as a substrate. Accordingly, when the RNA aptamer introduced with 2'-OMe, 2'-N$_3$ or the like is synthesized, the use of the mutant T7 polymerase Y639F/H784A, the mutant T7 polymerase H784A, etc. is preferable (Nucleic Acids Res. 30(24):138, 2002).

Also, the modification at the phosphate position includes modification in which a phosphate is modified with P(O)S ("thioate"), P(S)S ("dithioate"), P(O)NR$_2$ ("amidate"), P(O)R, P(O)OR', CO or CH$_2$ ("formacetal"). Here, R or R' is independently H or substituted or unsubstituted alkyl, the substituted or unsubstituted alkyl (especially alkyl having 1 to 20 carbon atoms) including an ether (—O—) bond, aryl, alkenyl, cycloalkyl, cycloalkenyl or aralkyl. A connector upon modification at the phosphate position includes —O—, —N—, —S— or —C—, and adjacent nucleotides are bound to each other using the connector.

The modification at the base position includes 5-position modification of pyrimidine, 8-position modification of purine, 4- or 5-position modification of uracil, exocyclic amine modification of cytosine, etc. Specifically, examples of the 5-position modification of pyrimidine may include benzyl carboxamide, benzyl aminocarbonyl, naphthylmethyl carboxamide, naphthyl methyl aminocarbonyl, tryptaminocarboxyamide, tryptaminocarbonyl and the like, and examples of the 4- or 5-position modification of uracil may include introduction of =S to the 4-position of uracil (4-thio uracil), introduction of —Br to the 5-position of uracil (5-bromo uracil), and introduction of —I to the 5-position of uracil (5-iodo uracil).

Regarding the modification at the base position, reference may be made to U.S. Pat. Nos. 5,719,273, 5,660,985 and the like. In particular, U.S. Pat. No. 5,660,985, entitled "High Affinity Nucleic acid ligands Containing Modified Nucleotides", discloses a method of selecting an aptamer including a nucleotide modified at the base position, having high affinity to a target molecule, through a SELEX process.

The RNA aptamer of the present invention may also be modified at the 5' end and/or the 3' end. For example, the 5' end may be modified with —NH$_2$ derived from 5'-hexylamine linker phosphoramidite. Alternatively, for example, the 3' end may be modified (3'-capped) with an inverted thymidine to form a 3'-3' linkage.

The RNA aptamer of the present invention may be modified by connecting polyalkylene glycol ("PAG") via a linker or without a linker. The linker is not particularly limited, so long as it is able to sufficiently function as a linker. Typically, amine (R—NH$_2$), activated ester (R'C(=O)OR"), anhydride (R'C(=O)OC(=O)R"), amide (R'(C=O)NR) or the like may be used as the linker.

Polyalkylene glycol is known in the art to improve the half-life of the aptamer in the blood by preventing renal filtration.

The PAG of the present invention typically has a molecular weight ranging from 5 kDa to 100 kDa, but may have a molecular weight in any range selected in consideration of the disease to which the aptamer of the present invention may be applied, the dosage form, and the route of administration. Generally, the molecular weight thereof falls in the range of 10 kDa to 80 kDa, and preferably 30 kDa to 50 kDa.

A typical example of PAG is polyethylene glycol ("PEG"). It is known that PEG not only reduces renal filtration but also causes neither toxicity nor immunogenicity. PEG may be used in any form or structure, such as a linear, branched or multi-branched form, without any particular limitation.

Regarding the introduction of "PAG" including PEG to the nucleic acid such as an aptamer, reference may be made to US 2004/0180360, entitled "Multivalent aptamer therapeutics with improved pharmacodynamic properties and methods of making and using the same".

There are known substitutes for PAG and PEG in the art, which have the same actions as PAG and PEG, such as increasing the half-life of the aptamer in the blood and reducing renal filtration. Such substitutes may be used for modification of the aptamer of the present invention, and examples of the substitutes may include polyoxazoline (POZ), polyPEG, hydroxyethyl starch (HES), albumin, lipophilic compounds such as cholesterol, etc. The substitute may bind to the aptamer of the present invention via a linker or without a linker.

The synthesis of the aptamer of the present invention is known in the art as described above, and examples thereof may include a solid-phase oligonucleotide synthesis process, a solution-phase synthesis process such as a triester synthesis process and the like, which are disclosed in the paper [Nucl. Acid Res. 14:5399-5467, 1986], the paper [Tet. Lett. 27:5575-5578, 1986], the paper [Nucl. Acid Res. 4:2557, 1977], and the paper [Lett., 28:2449, 1978].

Since the aptamer of the present invention binds to TNF-α to thus have TNF-α inhibitory activity, a pharmaceutical composition for the prevention or treatment of TNF-α-mediated disorders and diseases, containing the same as an active ingredient, may be produced.

In the pharmaceutical composition of the present invention, the aptamer of the present invention, which is an active ingredient thereof, may be contained in any suitable amount (effective amount) depending on the disease to which it is applied, the dosage form, the route of administration, etc., so long as it may exhibit TNF-α inhibitory activity and prophylactic and therapeutic efficacies against TNF-α-mediated disorders and diseases. A typical effective amount will be determined within the range from 0.001 wt % to 20.0 wt % based on the total weight of the composition. As used herein, the term "effective amount" refers to the amount of active ingredient contained in the composition of the present invention, which may exhibit an intended medical or pharmacological effect, such as an effect of ameliorating the TNF-α-mediated disease when the composition of the present invention is administered to a mammal, preferably a human, during the administration period suggested by medical professionals or the like. Such an effective amount may be determined experimentally within the ordinary skill of those skilled in the art.

The pharmaceutical composition of the present invention may be provided in the form of an oral or parenteral formulation depending on the route of administration by typical methods known in the art, including a pharmaceutically acceptable carrier in addition to the active ingredient. Here, the route of administration may be any suitable route including local routes, oral routes, intravenous routes, intramuscular routes, and direct absorption through mucosal tissue, and combinations of two or more routes may also be used. An example of a combination of two or more routes is a combination of two or more drug formulations depending on the route of administration, for example, the case in which one drug is primarily administered intravenously and another drug is secondarily administered via a local route.

The pharmaceutically acceptable carrier is well known in the art depending on the route of administration or dosage form, and reference may be made to the pharmacopoeia of each country, including the "Korean Pharmacopoeia".

When the pharmaceutical composition of the present invention is prepared in an oral formulation, it may be formulated into powders, granules, tablets, pills, sugar-coated tablets, capsules, solutions, gels, syrups, suspensions, wafers, and the like, in accordance with methods known in the art, together with an appropriate carrier. Here, examples of the appropriate carrier may include saccharides such as lactose, glucose, sucrose, dextrose, sorbitol, mannitol, xylitol, etc., starch such as corn starch, potato starch, wheat starch, etc., celluloses such as cellulose, methyl cellulose, ethyl cellulose, sodium carboxymethyl cellulose, hydroxypropylmethyl cellulose and the like, polyvinyl pyrrolidone, water, methylhydroxybenzoate, propylhydroxybenzoate, magnesium stearate, mineral oil, malt, gelatin, talc, polyol, vegetable oil, ethanol, glycerol and the like. Upon formulation, suitable binders, lubricants, disintegrants, coloring agents, diluents and the like may be included as needed. Examples of the appropriate binders may include starch, magnesium aluminum silicate, starch paste, gelatin, methylcellulose, sodium carboxymethylcellulose, polyvinylpyrrolidone, glucose, corn sweetener, sodium alginate, polyethylene glycol, wax and the like, examples of the lubricants may include sodium oleate, sodium stearate, magnesium stearate, sodium benzoate, sodium acetate, sodium chloride, silica, talc, stearic acid, magnesium and calcium salts thereof, polyethylene glycol, and the like, and examples of the disintegrants may include starch, methylcellulose, agar, bentonite, xanthan gum, starch, alginic acid or sodium salts thereof, and the like. Also, examples of the diluents may include lactose, dextrose, sucrose, mannitol, sorbitol, cellulose, glycine and the like.

When the pharmaceutical composition of the present invention is prepared in a parenteral formulation, it may be formulated in the form of injections, transdermal administrations, nasal aspirates and suppositories in accordance with methods known in the art, together with an appropriate carrier. As an appropriate carrier for an injection formulation, an aqueous isotonic solution or a suspension may be used, and specific examples thereof may include isotonic solutions such as PBS (phosphate-buffered saline) containing triethanolamine, sterile water for injection, 5% dextrose, and the like. Also, when formulated in the form of transdermal administrations, the pharmaceutical composition of the present invention may be formulated into ointments, creams, lotions, gels, liquids for external use, pastes, liniments, aerosols, and the like. Also, for nasal aspirates, the pharmaceutical composition of the present invention may be formulated in the form of an aerosol spray using an appropriate propellant such as dichlorofluoromethane, trichlorofluoromethane, dichlorotetrafluoroethane, carbon dioxide, etc., and for suppositories, a carrier such as Witepsol, Tween 61, polyethylene glycols, cacao butter, laurin fat, polyoxyethylene sorbitan fatty acid esters, polyoxyethylene stearates, sorbitan fatty acid esters, etc. may be used.

The pharmaceutical composition of the present invention may also be administered in the form of a liposome drug delivery system, such as a small unilamellar vesicle, a large unilamellar vesicle and a multi-lamellar vesicle. A liposome may be prepared from a variety of phospholipids including cholesterol, stearylamine or phosphatidylcholine. A liposome drug delivery system is known in the art, and reference may be made to, for example, U.S. Pat. No. 5,262,564.

With regard to the formulation of other pharmaceutical compositions and the preparation thereof, reference may be made to the paper that is well known in the art, such as [Remington's Pharmaceutical Sciences (19$^{th}$ ed., 1995)], etc.

The amount of the pharmaceutical composition according to the present invention, when administered, may fall in the range of 0.001 mg/kg/day to 1,000 mg/kg/day, and preferably 0.001 mg/kg/day to 1 g/kg/day, depending on the condition, weight, gender and age of the patient, the severity of the disease of the patient, and the route of administration. For example, upon oral administration, the dose may fall in the range of about 0.05 mg/kg/day to 7,500 mg/kg/day. The administration may be carried out once a day or several times a day. The dose is merely set forth for illustrative purposes, and does not in any way limit the scope of the present invention.

Advantageous Effects

As described above, according to the present invention, an aptamer binding to TNF-α and the use thereof for the prevention and treatment of TNF-α-mediated diseases can be provided.

DETAILED DESCRIPTION

Figure 1A:
FIG. 1A and FIG. 1B schematically show the secondary structures of TNF-α aptamers ATK001 (a) and ATK007 (b)
Figure 1B:
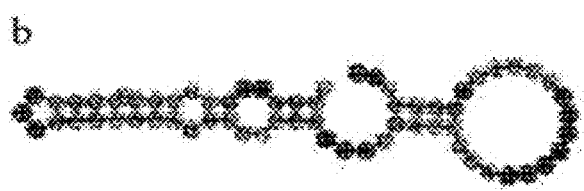

A better understanding of the present invention will be given through the following examples. However, these examples are not to be construed as limiting the scope of the present invention.

<Example 1> Preparation of RNA Aptamer Library

In order to prepare two groups of RNA libraries required to carry out a SELEX process, two kinds of single-stranded DNA oligonucleotides were constructed, each including a random base sequence as shown below.

5'-GGGAGGACGATGCGGC-Nn-AGACGACTCGCCCGA-3'
[Oligonucleotide 1]

5'-GCGGAAGCGTGCTGGG-Nn-CACATAACCCAGAGGTCGAT-3'
[Oligonucleotide 2]

The 5' and 3' underlined regions are fixed regions, to which a forward primer and a reverse primer are bound, respectively, and Nn is a sequence in which n bases including adenine (A), guanine (G), thymine (T), and cytosine (C) are randomly present. The forward primer is configured such that a T7 RNA polymerase promoter sequence for RNA synthesis is bound to the 5' end.

Two groups of DNA libraries were prepared by performing PCR using each of the two kinds of single-stranded DNA oligonucleotides as a template.

Particularly, 1,000 pM DNA single-stranded oligonucleotides, 2,500 pM PCR primer, 50 mM KCl, 10 mM Tris-Cl (pH 8.3), 3 mM $MgCl_2$, and 0.5 mM dNTP (dATP, dCTP, dGTP, and dTTP) were mixed, 0.1 U Taq DNA polymerase (Perkin-Elmer, Foster City Calif.) was added thereto, and PCR was performed through 32-cycle reactions under conditions of 95° C. for 30 sec, 55° C. for 30 sec and 72° C. for 1 min, followed by purification using a QIAquick-spin PCR purification column (QIAGEN Inc., Chatsworth Calif.).

Two groups of RNA libraries were prepared through in-vitro transcription using T7 RNA polymerase and using, as a template, each of the two groups of DNA libraries prepared above. As such, 2'F-CTP and 2'F-UTP, including ATP and GTP and 2'-F-substituted pyrimidine, were used to impart resistance to RNase.

Particularly, a 200 pM DNA library, 0 mM Tris-Cl (pH 8.0), 12 mM $MgCl_2$, 5 mM DTT, 1 mM spermidine, 0.002% Triton X-100, 4% PEG 8000, 5 U T7 RNA polymerase, 1 mM ATP and GTP, and 3 mM 2'F-CTP and 2'F-UTP were mixed and reacted at 37° C. for 6 hr. Thereafter, treatment with DNaseI (Promega), reaction at 37° C. for 30 min to remove the DNA template, and then purification using a Bio-Spin 6 chromatography column (Bio-Rad Laboratories, Hercules Calif.) were performed. The amount of nucleic acids and the purity thereof were determined using a UV spectrometer.

<Example 2> Isolation and Sequencing of Aptamer Binding to Human TNF-α

An aptamer binding to human TNF-α was isolated using a SELEX process.

The $10^{14}$ sequence/L single-stranded RNA library solution synthesized above was heated at 80° C. for 10 min at a concentration of 200 pM/200 μL in a SELEX buffer (50 mM Tris-Cl (pH 7.4), 5 mM KCl, 100 mM NaCl, 1 mM $MgCl_2$, 0.1% $NaN_3$), and then allowed to stand in ice for 10 min. Yeast tRNA (available from Life Technologies) having a concentration five times that of the single-stranded nucleic acid that was used and 0.2% BSA (bovine serum albumin, available from Merck) were added thereto, thus preparing a reaction solution.

Biotinylation of human TNF-α was performed in accordance with the protocol of a Protein Labeling kit (made by Jena Bioscience, Germany). A 1 M sodium bicarbonate solution in distilled water and a 10 mg/mL biotin solution in DMF (dimethylformamide) were prepared. Recombinant human TNF-α (Sigma-Aldrich, Germany) was added with the 1 M sodium bicarbonate solution, thus preparing a human TNF-α solution in which the final concentration of sodium bicarbonate was 100 mM and the final concentration of human TNF-α was 10 mg/mL. The human TNF-α solution and the biotin solution were mixed in equal amounts and reacted at room temperature for 1 hr, after which 2.5 mL of the reaction solution was placed in a Sephadex G-25 column (Sigma-Aldrich, Germany) and allowed to react for 10 min, followed by centrifugation at 10,000×g for 10 min to remove free biotin from the supernatant, thereby affording biotinylated human TNF-α.

The SELEX buffer reaction solution including the single-stranded RNA prepared as described above was added with 10 μg/mL of the biotinylated human TNF-α and allowed to react for 30 min, thus forming single-stranded RNA-TNF-α complexes, which were then separated in accordance with the protocol of Dynabeads M-280 Streptavidin (Invitrogen, USA). Particularly, the biotinylated human TNF-α-single-stranded nucleic acid complexes obtained by reacting the biotinylated human TNF-α with the single-stranded nucleic acids were added with Dynabeads M-280 streptavidin and reacted, thus forming biotinylated human TNF-α-single-stranded RNA-bead complexes through bonding of the biotin of the complexes and the avidin of the beads, which were then washed with a SELEX buffer (1×PBS, 1 mM magnesium acetate, pH 7.0), thereby yielding biotinylated human TNF-α-single-stranded RNA-bead complexes using a magnetic material.

RT-PCR was performed using the complexes thus obtained, whereby a DNA pool was amplified from the single-stranded RNA binding to human TNF-α.

Particularly, the complexes obtained above were added with 500 nM primer, denatured at 65° C. for 5 min, and allowed to stand at room temperature for 10 min, whereby RNA and the primer were bound to each other. Then, 1 mM dNTP, 5×RT buffer, and 25 U AMV RTase (Promega) were added thereto, reacted at 37° C. for 30 min, heated at 95° C. for 5 min, and cooled at 4° C., thus inactivating the reverse transcriptase. The synthesized cDNA was mixed with 2,500 pM PCR primer, 50 mM KCl, 10 mM Tris-Cl (pH 8.3), 3 mM $MgCl_2$, and 0.5 mM dNTP (dATP, dCTP, dGTP, and dTTP), after which 0.1 U Taq DNA polymerase (Perkin-Elmer, Foster City Calif.) was added thereto, and PCR was performed through 32-cycle reactions under conditions of 95° C. for 30 sec, 55° C. for 30 sec and 72° C. for 1 min to prepare DNA, which was then identified in a 3% agarose gel. Further, the RNA synthesis through in-vitro transcription in the same manner as that for preparing the RNA library and the selection as described above were repeated three times.

DNA obtained by RT-PCR and PCR was cloned into a T-vector to obtain single clones, and the base sequences were analyzed using these single clones to obtain 25 RNA sequences including the RNA of SEQ ID NO: 1 ("ATK001") from the RNA library derived from [Oligonucleotide 1] and 37 RNA sequences including the RNA of SEQ ID NO: 2 ("ATK007") derived from [Oligonucleotide 2]. Each single-stranded RNA for use in subsequent experiments was prepared through in-vitro transcription in the same manner as described above from the DNA, the sequences of which were identified.

<Example 3> Measurement of Binding Affinity of RNA Aptamer Through Plate-Based Binding Assay Through a plate-based binding assay, the binding of the single-stranded RNA to human TNF-α was measured.

Figure 2:
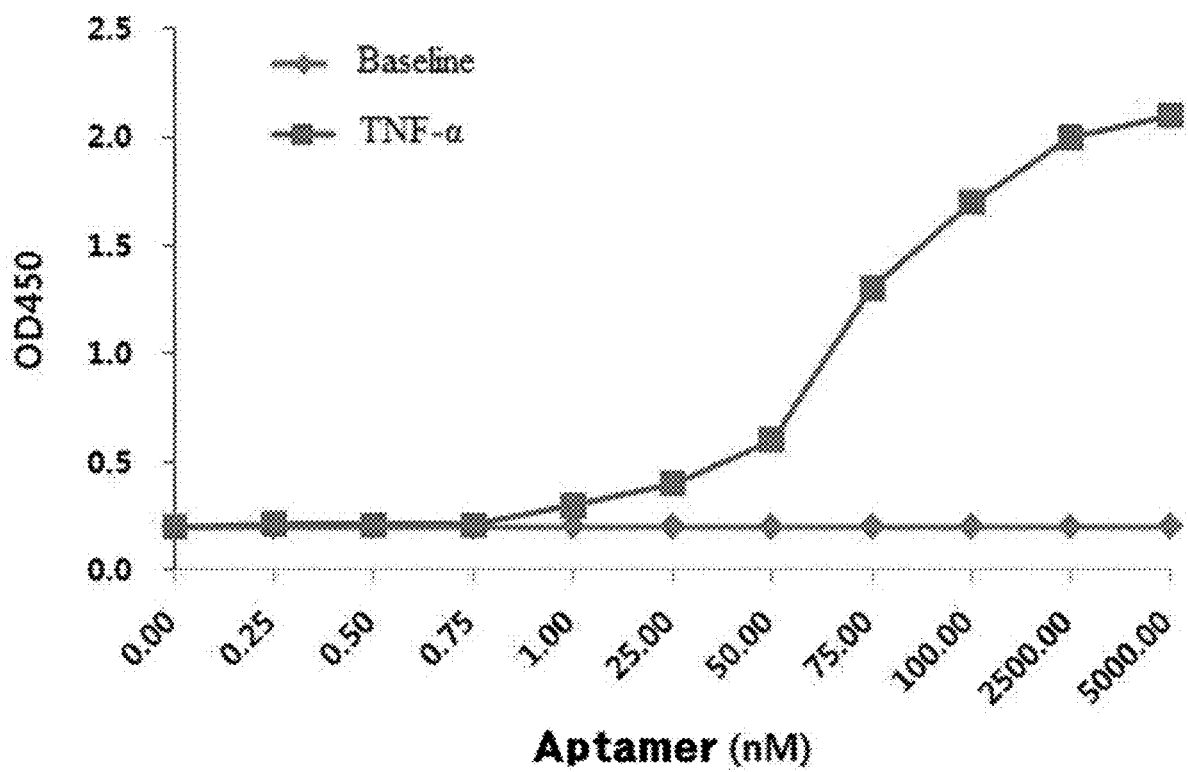
FIG. 2 is a graph showing the results of measurement of the amount of TNF-α aptamer ATK007 bound to human TNF-α through plate-based binding assay.

In order to investigate the binding affinity of the single-stranded RNA, the sequence of which was identified in <Example 2> above, to TNF-α, 0.5 mg/ml recombinant human TNF-α protein was diluted with DPBS (Dulbecco's Phosphate-buffered Saline) to yield a final concentration of 15 μg/mL, and 100 μL thereof was added to a 96-well Maxisorb plate and cultured at 4° C. overnight. Thereafter, the TNF-α solution was removed, and the plate was then washed three times at room temperature using 2004 of a washing buffer (DPBS+0.05% Tween 20). Thereafter, the plate was blocked at room temperature for 30 min with 200 μL of 10 mg/mL BSA (bovine serum albumin) dissolved in DPBS. Thereafter, the BSA blocking solution was removed, and washing was performed three times with 200 μL of a washing solution. The single-stranded RNA subjected to serial dilution with 0.1% BSA in DPBS was added to the above plate and cultured at room temperature for 3 hr. Then, washing was performed three times with 200 μL of a washing buffer, after which 100 μL of a 0.5 μg/ml rabbit single-clone TNF-α antibody (Epitomics, USA) was added to the above plate and cultured at room temperature for 60 min. Then, the TNF-α antibody solution was removed, and the plate was washed three times with 200 μL of a washing buffer. Thereafter, 100 μL of an anti-rabbit IgG-HRP secondary antibody (Cell Signaling Technology), 1000-fold diluted with an assay buffer, was added to each well and cultured for 30 min. Then, washing was performed three times with 200 μL of a washing buffer, after which 100 μL of a TMB solution (Pierce) was added to each well and cultured for 2 min, and 100 μL of a stop solution (2N $H_2SO_4$) was added to each well, and thus the reaction was terminated. Thereafter, the plate was measured at 450 nm using a Victor$^3$V 1420 multilabel counter (Perkin Elmer). Based on the measurement results, ATK001 or ATK007, among the single-stranded nucleic acids the sequences of which were identified in <Example 2>, was confirmed to exhibit the highest binding affinity to recombinant human TNF-α. Through five repeated experiments on ATK001 or ATK007, it was confirmed that the average binding affinities of ATK001 and ATK007 to recombinant TNF-α were 43 nM and 30 nM, respectively. Data on ATK001 obtained from one of these experiments is shown in [FIG. 2].

<Example 4> Measurement of RNA Aptamer Binding Affinity Through SPR Analysis

SPR (Surface Plasmon Resonance) analysis was performed using a Biacore2000 (BIACORE, USA). A mixture of NHS (0.1 M N-hydroxysuccinimide) and DEC (0.4 M N-ethyl-N'-(dimethylaminopropyl)carbodiimide) in equal amounts (50 μL) was prepared and allowed to flow at 5 μL/min for 40 sec to thus activate a CM5 sensor chip. When 150-200 RU appeared, TNF-α protein to be immobilized was mixed with sodium acetate (pH 4.0) and allowed to flow at 50 ng/L. In order to evaluate whether or not the protein was immobilized, 50 mM NaOH was allowed to flow for 5 sec. At 80° C., RNA aptamers ATK001 and ATK007 were denatured for 5 min and then restored at room temperature for 15 min, thus preparing an analyte (RNA).

In order to determine kinetics, the flow rate was changed to 30 μL/min. The analyte prepared above was dissolved in 1×HBS so as to have a concentration ranging from 6.25 nM to 500 nM, and was allowed to flow to the sensor chip, and thus the binding affinity between the selected RNA aptamer and the TNF-α protein was quantified using an equilibrium dissociation constant Kd.

The equilibrium dissociation constant Kd was calculated using a kinetic simultaneous Ka/Kd model program from the plot curve of the Req value obtained from a sensorgram after setting of 1:1 binding of the selected RNA aptamer to TNF-α.

Figures 3A, 3B:
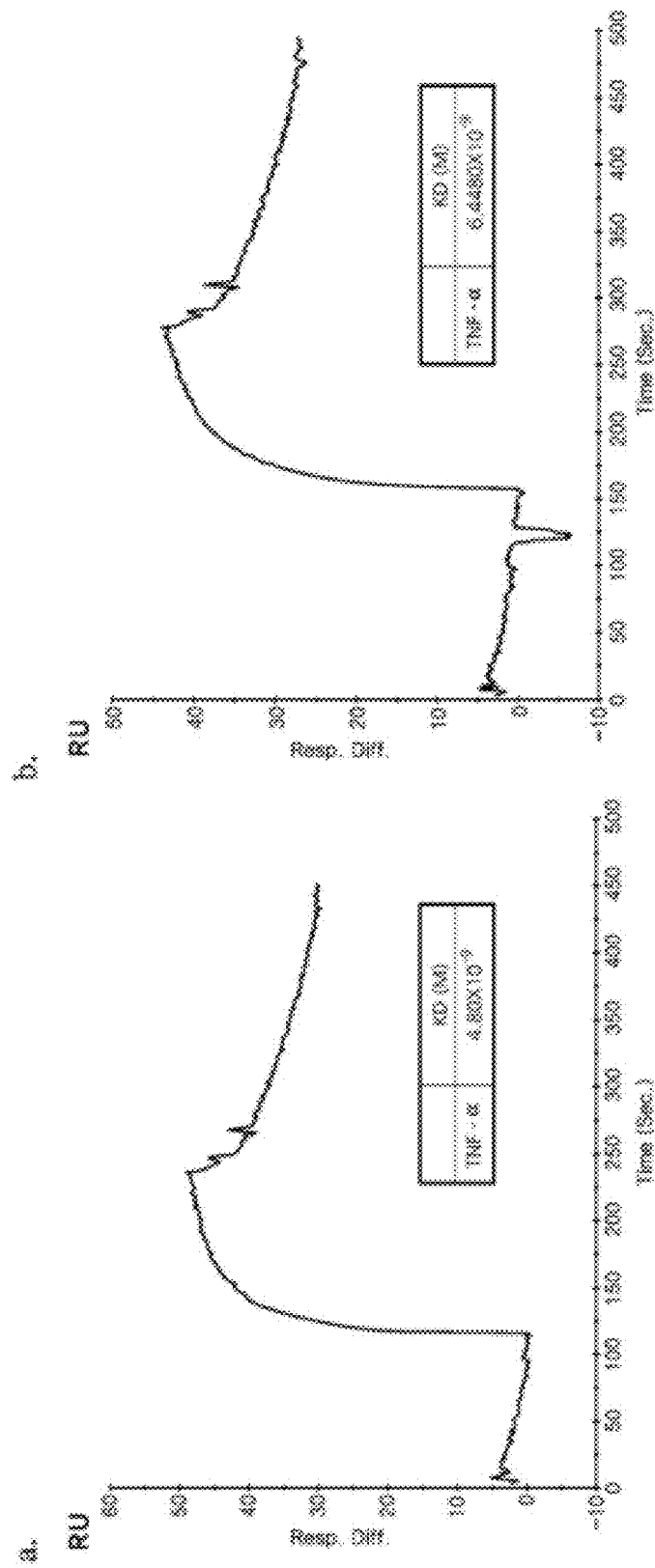
FIG. 3A and FIG. 3B show sensorgrams and dissociation constants of TNF-α aptamers ATK001 (a) and ATK007 (b) and human TNF-α using an SPR process.

As a result, the calculated Kd values of the ATK001 and ATK007 aptamers in the single-stranded nucleic acids binding to TNF-α selected in <Example 2> were in the range of 4.0 to 7.0 nM, as shown in [FIG. 3], indicative of strong binding capability.

<Example 5> Measurement of RNA Aptamer Binding Affinity Through Gel Retardation

The single-stranded nucleic acids (50 pM) binding to TNF-α, selected in <Example 2> and labeled with radio-isotopes, were reacted with TNF-α protein in a manner in which the amount of TNF-α protein was increased (ranging from 0 to 320 nM). Here, the total amount of the aptamer, TNF-α protein, binding buffer (30 mM Tris-HCl (pH 7.5), 150 mM NaCl, 1.5 mM $MgCl_2$, and 2 mM DTT), and 3 g tRNA was adjusted to 40 μL, followed by binding at room temperature for 30 min. 6×BPB was added thereto, after which electrophoresis at 4° C. and 120 V using a 6% native gel (6% polyacrylamide, 1×TBE, 10 mM $MgCl_2$, 2% glycerol), exposure to an X-ray film and development were performed. The dissociation constant Kd was determined by calculating the amount of the RNA aptamer binding to TNF-α relative to the total RNA aptamer.

Through such experiments, after reaction of the radioisotope-labeled RNA and the TNF-α protein in a manner in which the amount of TNF-α protein was increased, the amount thereof, the position of which was changed on a 4% non-denatured acrylamide gel, was measured. The results are shown in [FIG. 4].

Figure 4A:
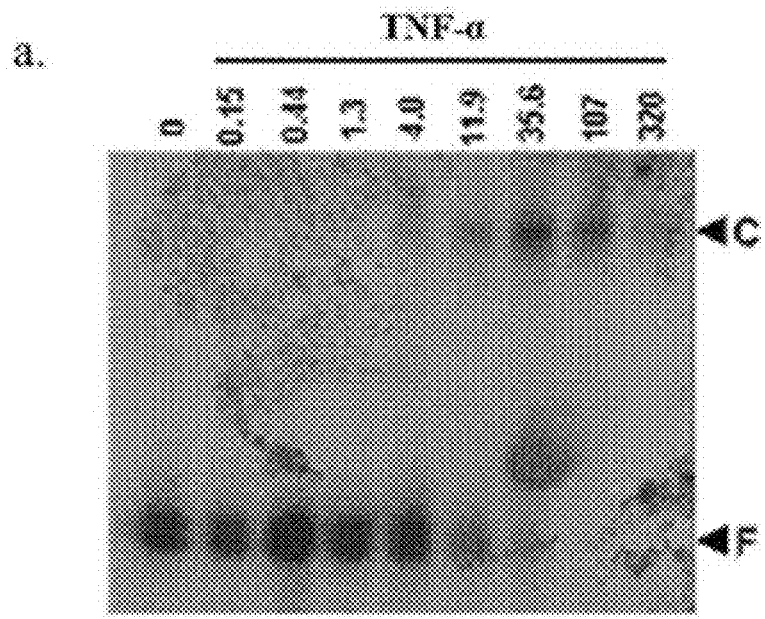
FIG. 4A, FIG. 4B and FIG. 4C show the results of analysis of TNF-α aptamers ATK001 (a) and ATK007 (b) through gel retardation and a graph showing the percentage of the aptamer bound to TNF-α (c)
Figure 4B:
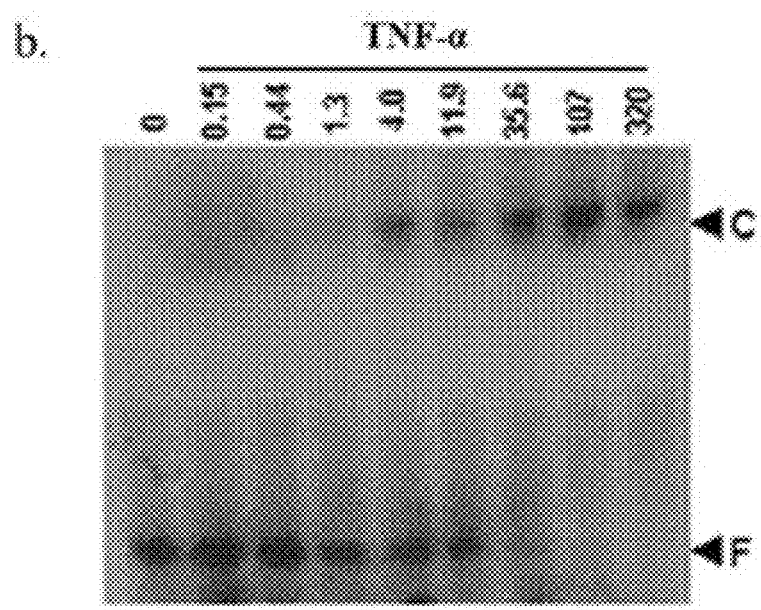
Figure 4C:
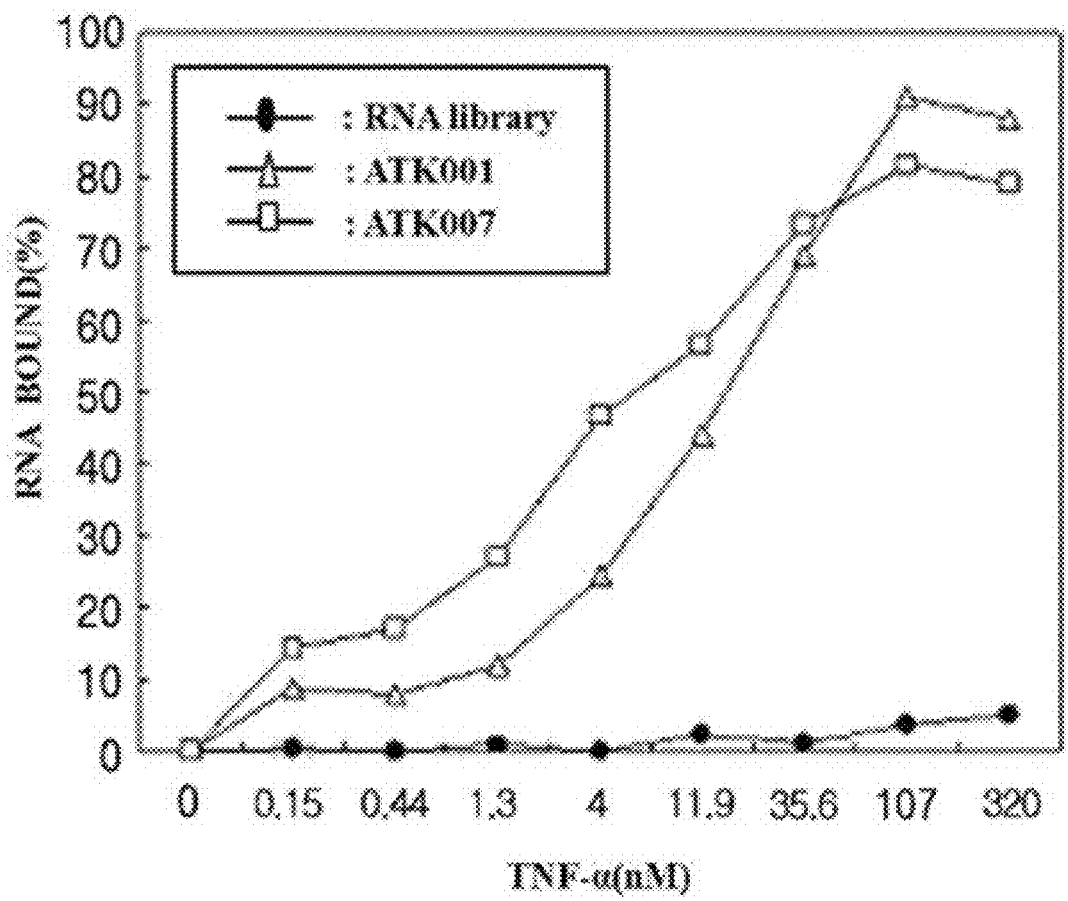

The 4% non-denatured acrylamide gel images of the TNF-α-bound RNA aptamer (C) and the TNF-α-unbound RNA aptamer (F), resulting from reacting the radioisotope-labeled 50 pM RNA aptamer ATK001 (a) and 50 pM RNA aptamer ATK007 (b) with TNF-α in a manner in which the amount of TNF-α was increased (ranging from 0 to 320 nM), are shown in a and b of FIG. 4. The percentage of RNA binding to TNF-α was determined and is graphed in c of FIG. 4. This result is the average of the measurement values of three repeated experiments.

As shown in FIG. 4, RNA aptamers ATK001 and ATK007 both bind to TNF-α in a dose-dependent manner, thus forming efficient positional changes and showing dissociation constants Kd with high affinities of about 18 nM and 5 nM, respectively. In particular, ATK001, which is selected, is able to bind to the target protein about 1.2 times more strongly than ATK007 to thus exhibit more efficient binding capability.

Figure 5A:
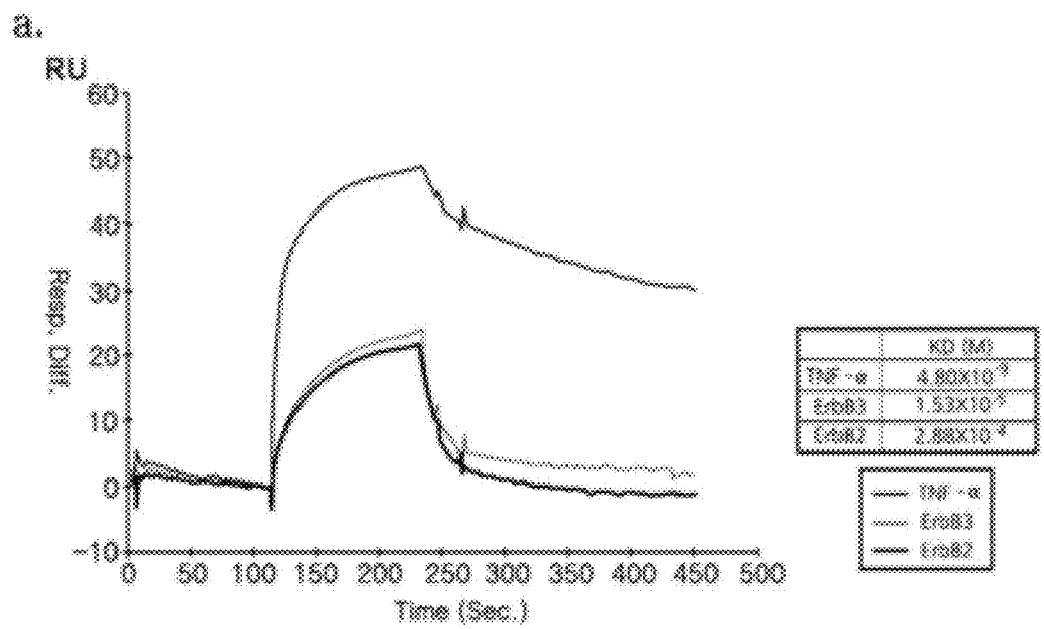
FIGS. 5A, 5B, and 5C show sensorgrams (a) of TNF-α aptamer ATK001 and human TNF-α, ErbB2 and ErbB3, sensorgrams (b) of TNF-α aptamer ATK007 and human TNF-α, ErbB2 and ErbB3, using an SPR process, and sensorgrams (c) of TNF-α aptamer ATK007 and IGF-BP1 and individual dissociation constants.
Figure 5B:
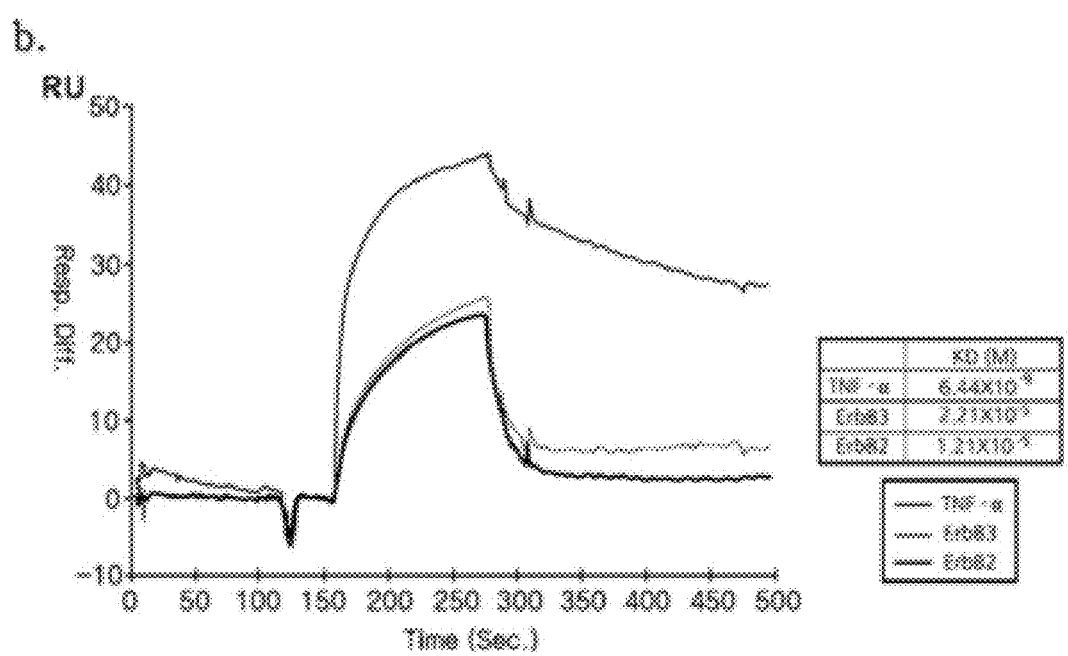
Figure 5C:
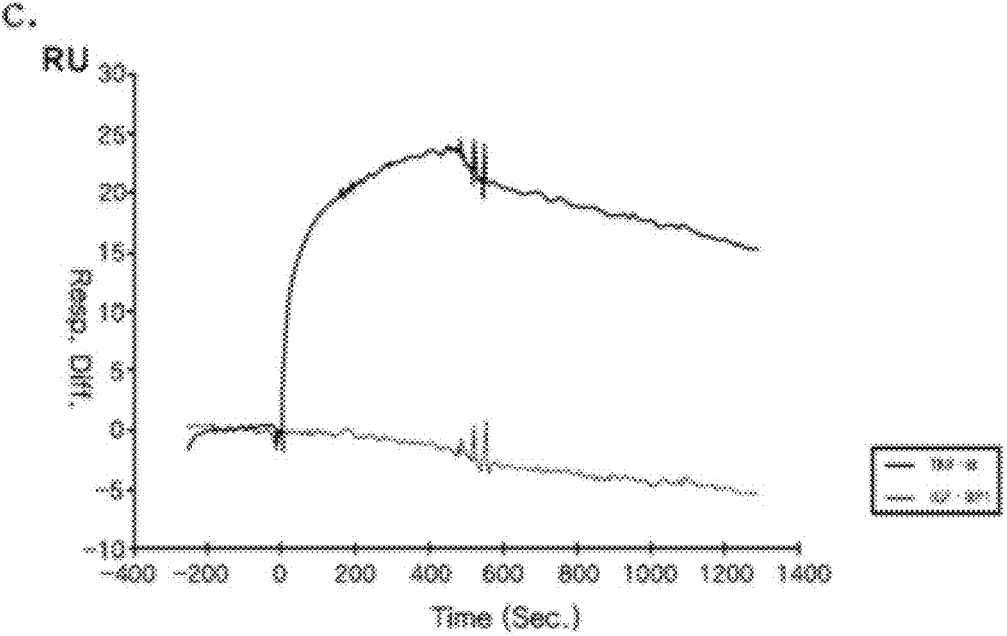

<Example 6> Measurement of Binding Specificity of RNA Aptamer Through SPR Analysis In order to evaluate the binding specificity of the RNA aptamer to TNF-α through SPR analysis in the same manner as in <Example 4> above, the binding capability to ErbB2 (ThermoFisher, USA) (Nucleic Acid Ther. 2011 June; 21(3): 173-178), ErbB3 (ThermoFisher, USA) (Proc. Natl. Acad. Sci. USA. (2012), 109(33):13237-42) and IGF-BP1 (ThermoFisher, USA) (Insulin-like growth factor-binding protein 1) (Crit. Rev. Oncol. Hematol. (2008), 66(2):91-98), in addition to TNF-α, was quantified in Kd. The results are shown in [FIG. 5] (FIG. 5a illustrating the results of measurement of binding capability of ATK001, FIG. 5b illustrating the results of measurement of binding capability of ATK007, and FIG. 5c illustrating the results of measurement of binding capability of ATK001).

As shown in [FIG. 5], the RNA aptamers ATK001 and ATK007 had binding capability of $10^{-9}$ M (nM) to TNF-α and binding capability of about $10^4$ nM to ErbB2 and ErbB3dp, and were seldom bound to IGF-BP1 (Insulin-like growth factor-binding protein 1), and thus appeared to have high binding capability to TNF-α.

<Example 7> Effect of TNF-α Aptamer on Transcription of Acute-Phase Protein, Angiogenic Substance and Proinflammatory Cytokine 24 hr before the experiment, SK-HEP1 (ATCC) liver cancer cells were seeded at a density of $1.0 \times 10^4$ into 96-well flat-bottom microtiter plates containing 10% FBS-added DMEM. 2 μg/mL aptamer (ATK001 or ATK007) or 20 μg/mL anti-TNF-α mAB (R&D systems) was reacted with human TNF-α (Invitrogen, USA) for 2 hr in PBS, and the resulting reaction product was added to wells of the plates containing the cells and cultured for 2 hr. Subsequently, the cells were washed with warm PBS and then cultured for an additional 48 hr in a complete medium. The cultured cells were collected, RNA was separated therefrom, and RT-PCR was performed with the primers of Tables 1 and 2 for acute-phase proteins, an angiogenic substance and proinflammatory cytokines. The PCR products were subjected to electrophoresis in an agarose gel to evaluate the effects of TNF-α aptamers ATK001 and ATK007 on the transcription of acute-phase proteins, an angiogenic substance and proinflammatory cytokines.

TABLE 1

Acute-phase protein gene and primer thereof

| Gene | Primer Sequence | Product Size (bp) |
|---|---|---|
| GAPDH | F: 5-TATCGGACGCCTGGTTAC-3<br>R: 5-TGCTGACAATCTTGAGGGA-3 | 407 |
| Hepato-globin | F: 5-CCTGAATGTGAAGCAGTATGT-3<br>R: 5-TTCTGTTTGAGTTTGATGAGC-3 | 338 |
| Fibrogen-gamma | F: 5-CTACTTCGCTGGTGGGGATG-3<br>R: 5-GCTTTGCAAGTCCATTGTCCA-3 | 493 |
| Fibronectin | F: 5-CCGTGGGCAACTCTGTC-3<br>R: 5-TGCGGCAGTTGTCACAG-3 | 438 |
| Transferrin | F: TGGAGACAGATGCTCCCTCC-3<br>R: TTTGTGCTCTGTGTATGTGGTAAGG-3 | 119 |
| Ferritin-L | F: 5-GAGACCACAAGCGACCCGCA-3<br>R: 5-GAGGTGACGGAGGGCTGGCT-3 | 138 |

TABLE 2

Proinflammatory cytokine gene, angiogenic substance and primer thereof

| Gene | Primer Sequence | Product Size (bp) |
|---|---|---|
| GAPDH | F: 5-TATCGGACGCCTGGTTAC-3<br>R: 5-TGCTGACAATCTTGAGGGA-3 | 407 |
| TNF-α | F: 5-TTCTGTCTACTGAACTTCGGGGTGATCGGTCC-3<br>R: 5-GTATGAGATAGCAAATCGGCTGACGGTGTGGG-3 | 468 |
| IL-1β | F: 5-TGCGAATCTCCGACCACCACTACA-3<br>R: 5-TGGAGGTGGAGAGCTTTCAGTTCATAT-3 | 295 |

TABLE 2-continued

Proinflammatory cytokine gene, angiogenic substance and primer thereof

| Gene | Primer Sequence | Product Size (bp) |
|---|---|---|
| IL6 | F: 5-ATGAACTCCTTCTCCACAAGCGC-3<br>R: 5-GAAGAGCC- CTCAGGCTGGACTG-3. | 628 |
| VEGF | F: 5-GAGTATATCTTCAAGCCGTCCTGT-3<br>R: 5-ATCTGCATAGTGACGTTGCTCTC-3 | 230 |

Figure 6:
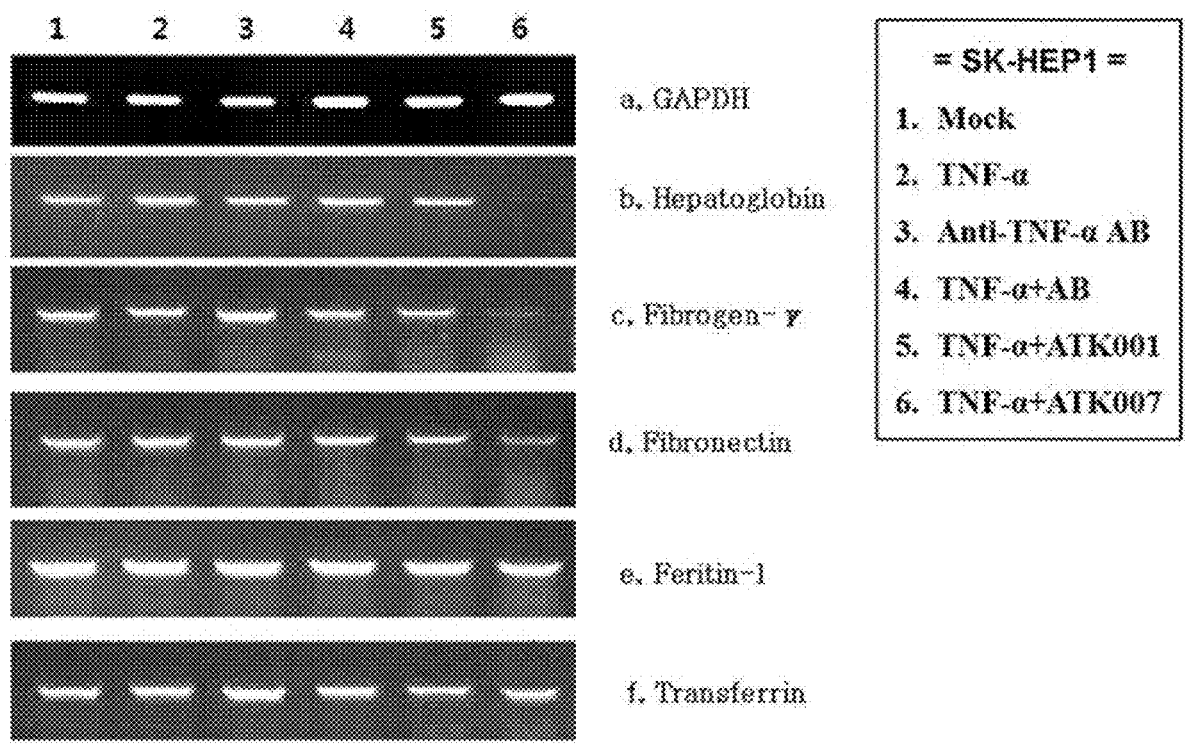
FIG. 6 shows the effect of TNF-α aptamer on expressing acute-phase proteins at the transcription level.

The results are shown in [FIG. 6]. As shown in [FIG. 6], the TNF-α aptamer used in the experiment suppressed expression at the transcription level of the acute-phase proteins (hepatoglobin, fibrogen-γ, fibronectin and transferrin), whose expression levels increased during the acute phase, and had little influence on the protein (ferritin-L), whose expression level decreased during the acute phase.

Figure 7:
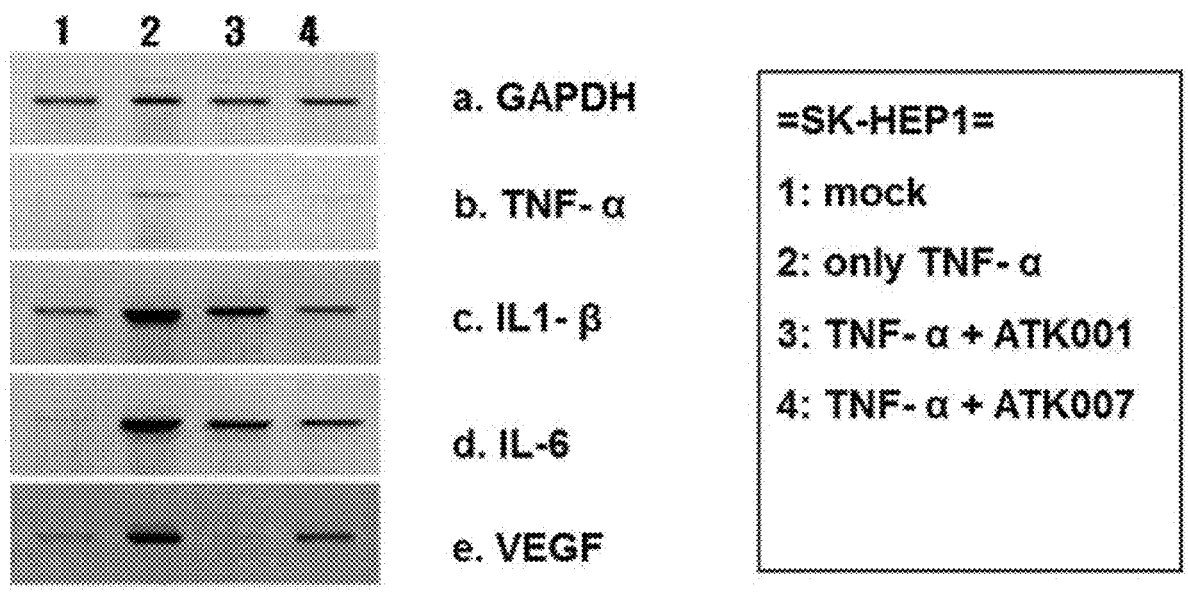
FIG. 7 shows the effect of TNF-α aptamer on expressing proinflammatory cytokines and an angiogenic substance at the transcription level.

As shown in [FIG. 7], the TNF-α aptamer used in the experiment was observed to suppress the expression at the transcription level of proinflammatory cytokines (TNF-α, IL-1β and IL6) and the angiogenic substance (VEGF), whose expression levels increased during the acute phase.

<Example 8> Effect of TNF-α Aptamer on NO Generation of Macrophage

RAW 264.7 cells (ATCC) were seeded at a density of $1.0 \times 10^5$ to wells of 12-well plates containing RPMI 1640 and 10% FBS. The cells were pretreated with 2 U/mL IFN-γ (Peprotech, N.J.) for 1 hr, after which a 100 ng/mL TNF-α-treated experimental solution was added to 1 mL of a medium containing the TNF-α aptamer (ATK001 or ATK007) having a final concentration of 2 μg/mL, a control RNA library having a final concentration of 2 μg/mL, or 10 μg/mL anti-TNF-α mAB. At each time point, 1004 of the medium was aliquoted, and $NO_2^-$ was analyzed using a reagent kit of Griess (Invitrogen, Carlsbad, Calif.). All experiments were performed three times in triplicates.

Figure 8:
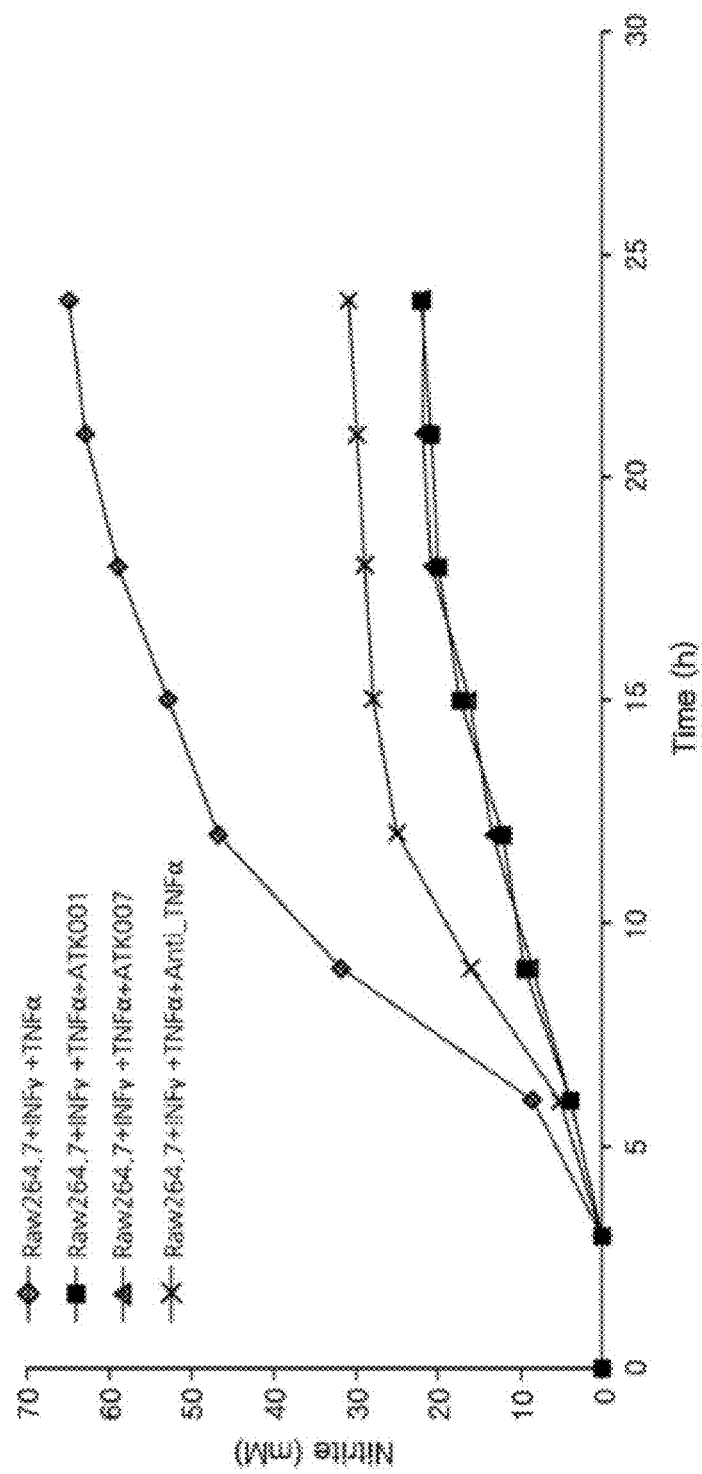
FIG. 8 shows the effect of TNF-α aptamers ATK001 and ATK007 on inhibiting NO generation.

The results are shown in [FIG. 8]. As shown in [FIG. 8], upon treatment with the TNF-α RNA aptamer ATK001 and the TNF-α RNA aptamer ATK007, NO generation was inhibited, and the TNF-α RNA aptamer ATK007 exhibited inhibitory activity similar to that of anti-TNF-α mAB.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. An RNA aptamer or a variant thereof, comprising SEQ ID NO: 1 or SEQ ID NO: 2 and binding to TNF-α.

2. The aptamer of claim 1, wherein the RNA aptamer is a modified aptamer, and the modified aptamer is an aptamer which is chemically modified in at least one position of a sugar position, a phosphate position, a base position, a 5' end position and a 3' end position of a ribonucleotide.

3. The aptamer of claim 2, wherein the modified aptamer is an aptamer modified at the sugar position, and the aptamer is configured such that at least one hydroxyl group of the sugar is modified with any one of a halogen group, an aliphatic group, an ether group, and an amine group.

4. The aptamer of claim 2, wherein the modified aptamer is an aptamer modified at the sugar position, and the aptamer is configured such that a 2'-OH group of the sugar is modified with any one of OMe, O-alkyl, O-allyl, S-alkyl, S-allyl and halogen.

5. The aptamer of claim 1, wherein the RNA aptamer is a modified aptamer, and the modified aptamer is configured such that all C and U of SEQ ID NO: 1 or SEQ ID NO: 2 are 2'-F-modified C and 2'-F-modified U, respectively.

6. The aptamer of claim 1, wherein the RNA aptamer is an aptamer modified at a phosphate position, and the modified aptamer is configured such that a phosphate is modified with P(O)S ("thioate"), P(S)S ("dithioate"), P(O)NR$_2$ ("amidate"), P(O)R, P(O)OR', CO or CH$_2$ ("formacetal").

7. The aptamer of claim 1, wherein the RNA aptamer is an aptamer modified at a base position, and the modified aptamer is configured such that a 5-position of pyrimidine, an 8-position of purine, a 4-position of uracil, a 5-position of uracil, or an exocyclic amine position of cytosine is modified.

8. The aptamer of claim 1, wherein the RNA aptamer is an aptamer modified at a 5' end position, and the modified aptamer is configured such that —NH$_2$ is bound to the 5' end.

9. The aptamer of claim 1, wherein the RNA aptamer is an aptamer modified at a 3' end position, and the modified aptamer is configured such that an inverted thymidine is bound to form a 3'-3'linkage.

10. The aptamer of claim 1, wherein the RNA aptamer is modified by connecting polyalkylene glycol via a linker or without a linker.

11. The aptamer of claim 1, wherein the RNA aptamer is modified by connecting polyethylene glycol via a linker or without a linker.

12. The aptamer of claim 11, wherein the RNA aptamer is modified through introduction of polyethylene glycol at a 5' end position using amine (R—NH$_2$) as a linker.

13. A pharmaceutical composition, comprising the aptamer of claim 1.

* * * * *